United States Patent [19]

Jacobi

[11] 4,011,142

[45] Mar. 8, 1977

[54] PROCESS FOR MEASURING THE PLASMINOGEN CONTENT OF A SAMPLE

[75] Inventor: Eckart Jacobi, Erkrath, Germany

[73] Assignee: Behring-Werke AG., Marburg, Germany

[22] Filed: Jan. 15, 1975

[21] Appl. No.: 541,335

[30] Foreign Application Priority Data

Jan. 27, 1973 Germany .......................... 2338254
June 29, 1974 Germany .......................... 2431342

[52] U.S. Cl. ........................................ 195/103.5 R
[51] Int. Cl.² ...................................... G01N 31/14
[58] Field of Search ............ 195/103.5 R; 23/230 B

[56] References Cited

UNITED STATES PATENTS 3,853,710 12/1974 Innerfield .................. 195/103.5 R

OTHER PUBLICATIONS

Hedner et al., "Comparison Between a Direct and Indirect Method for Determining Plasminogen," Thromb. Diath. Haemorrh., 26, (1971), pp. 289–294.

Flute, "The Assessment of Fibrinolytic Activity in the Blood," Brit. Med. Bull., vol. 20, No. 3, (1964), pp. 195–199.

Fletcher, "Pathological Fibrinolysis," Pro. Soc. Exptl. Biol. vol. 45, (1966 Jan.–Feb.), pp. 84–88.

*Primary Examiner*—A. Louis Monacell
*Assistant Examiner*—C. A. Fan
*Attorney, Agent, or Firm*—Malcolm W. Fraser

[57] ABSTRACT

The plasminogen content of a blood sample is measured by determining the rate of formation of fibrin in a sample in which antiplasmin-free plasminogen is activated to form plasmin before the onset of fibrin formation so that the plasmin-conditioned break-down of the fibrin occurs simultaneously with formation of fibrin.

8 Claims, 1 Drawing Figure

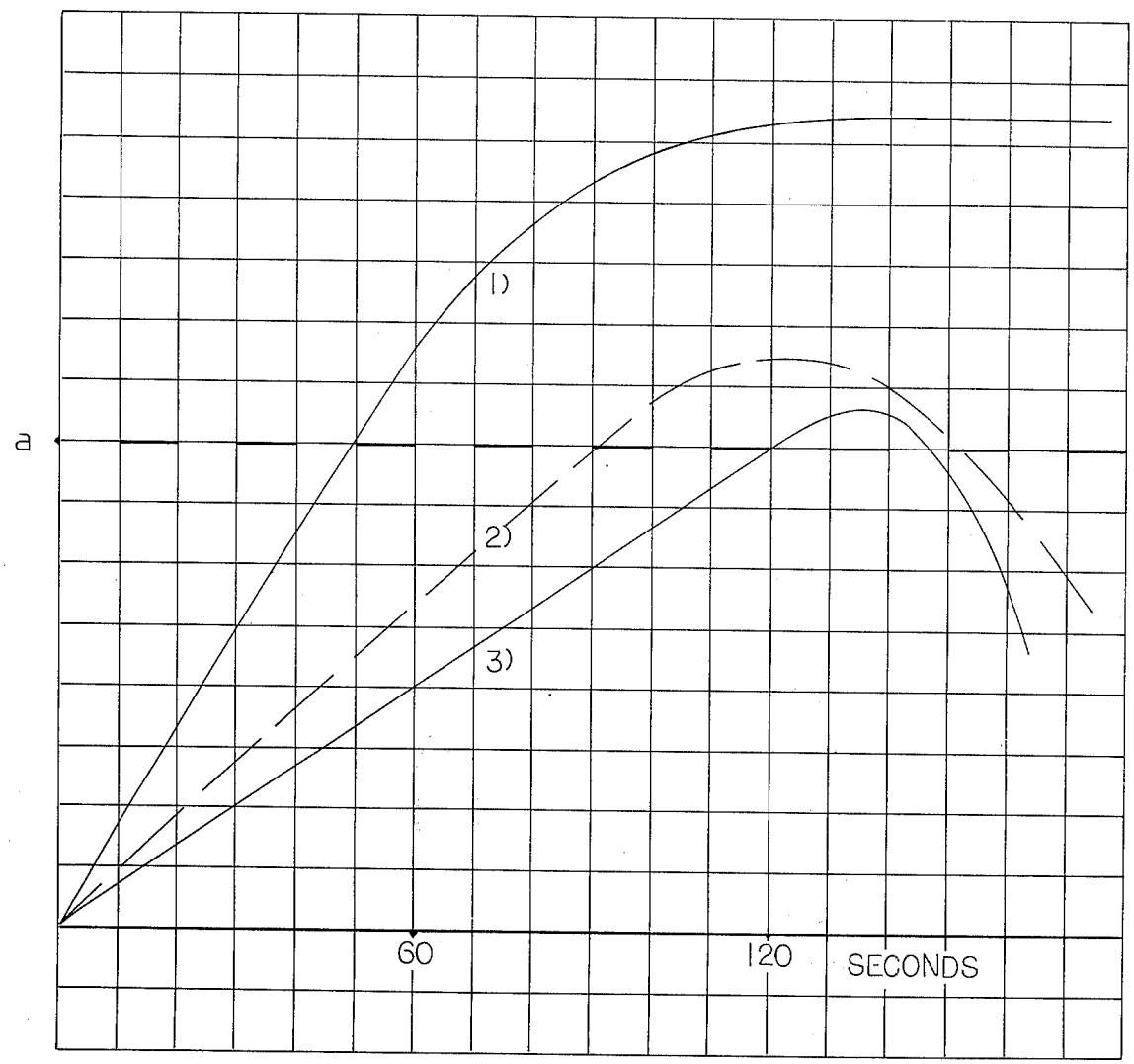

ORDINATE: Setting of the fibrincoagulum, a)
End point of measurement in the coagulometer ABSCISSA: Testing Time 1) Formation of fibrin with the addition of: Fibrinogen + Urokinase + Thrombin 2) Formation of fibrin with the addition of: Fibrinogen + Fibrinolysin (50% dilution) + Urokinase + Thrombin 3) Formation of fibrin with the addition of: Fibrinogen + Fibrinolysin (100% dilution) + Urokinase + Thrombin

PROCESS FOR MEASURING THE PLASMINOGEN CONTENT OF A SAMPLE

FIELD OF THE INVENTION

The invention relates to a process for measuring the plasminogen content of a sample and is concerned more particularly with the determination of the plasminogen content of a patient's blood. This is necessary in order to dose and to check the progress of fibrinolytic or antifibrinolytic therapy for thromboembolic invalids or for patients with coagulation disturbance illnesses.

BACKGROUND OF THE INVENTION

It is known that, in blood clotting, the soluble fibrinogen is converted by thrombin into the insoluble fibrin. Plasmin, which is present in the blood as plasminogen (prestage) and is blocked by antiplasmins, serves to break down the fibrin coagulum again.

On this basis, for example, it has become possible in recent years to dissolve blood clots by the plasmin activator streptokinase with the help of the body's own plasmin. With this therapy both thromboses as well as cardial infarcts have been treated successfully. The streptokinase treatment, however, has not been widely employed because the mortality rate has been too high. This is because routine plasminogen determination has not hitherto been possible and, with rising plasmin activation, the danger of a hemorrhage increases.

Various methods and apparatus for measuring the plasminogen content are indeed already known, for example the Clot Lysis Time Recorder, manufactured by Medicon Limited, Glasgow, Scotland; the Enzo-Diffusion Fibrin-plate test of Hyland, Travenol International GmbH, Munich, and the plasminogen plate test of Behringwerke, Marbur, Lahn. These methods are unsuitable for routine purposes because, on the one hand, they are expensive and on the other hand they require too much time, i.e. they usually take between 6 and 48 hours. With nearly all methods for determining the plasminogen content of a sample, the dissolution of the coagulated fibrin is measured and this, however, is only accessible to measurement with difficulty. Inter alia, the length of time the known methods take to perform depends on the difficulty of separating the antiplasmins from the plasminogen, which hitherto has only been incompletely accomplished.

SUMMARY OF THE INVENTION

This problem is solved according to the invention in that the plasminogen content is measured by determining the rate of formation of fibrin. This can be effected since the formation of fibrin in a solution of fibriongen and antiplasmin-free, plasminogen activated specimen plasma is retarded by adding thrombin and the plasminogen content can be established by determining retardation of the rate of coagulation.

With the invention, antiplasmin-free plasminogen, for example from a patient, is activated to form plasmin before the onset of fibrin formation, so that the plasmin-conditioned break-down of the fibrin (fibrinolysis) occurs simultaneously with the fibrin formation. The coagulation occurring with the fibrin formation is retarded by the plasmin effect and the rate of retardation of coagulation provides a measure for the plasminogen content.

In particular, according to the invention, the formation of fibrin is measured by determining the moment of its solidification, and the reduction in the plasminogen content is measured by comparing the normal moment of solidification with the moment of solidification with accelerated coagulation. Instead of determining the particular moments in time when the above events take place, the course of coagulation can be established.

Fibrin formation can be constantly predetermined by causing a constant quantity of fibrinogen to coagulate by a constant dose of thrombin. Measurement of the fibrin solidification presents no problem because apparatus for this purpose are available in the form of coagulometers (for example, that manufactured by Schnittger Gross). By washing citrate plasma with 3 parts of iso-amylalcohol, the entire antiplasmin activity is eliminated (see "The Significance of Plasma Inhibitor(s) in the Control of Fibrinolytic (Plasmin) Activity in Blood", by MONKHOUSE, F. C. et al., Thrombos. Diathes. haemorrh. 1972, 28, 367–375).

The process is designed in such a way that the speed of formation of the fibrin is slightly greater than the speed of decomposition. The process according to the invention will now be described in greater detail with reference to the accompanying graph.

BRIEF DESCRIPTION OF THE DRAWING

In the drawing, time is plotted on the abscissa, while the ordinate shows solidification or coagulation of the fibrin. The line drawn parallel to the abscissa, which is designated by $a$, signifies the final point of the measurement in the coagulometer.

The curve marked 1 shows the rate of formation of fibrin with a specimen consisting of a solution of fibrinogen, urokinase and thrombin (without plasmin). The measurement is designed in such a way that the rate of formation of the fibrin is slightly greater than the rate of decomposition. With normal plasminogen content (100%), curve 3 is produced, which shows the formation of fibrin with a specimen composed of fibrinogen, plasmin (100%), urokinase and thrombin. Curve 2 shows the formation of fibrin in a specimen consisting of fibrinogen, urokinase and thrombin, as well as plasmin with 50% dilution.

The graph shows that an evaluation of the plasminogen content is obtained by the determination of a reduction of the fibrin formation time which is sufficient for the desired accuracy of measurement. A calibration curve is obtained by plotting the measurement times, afforded by diluting specimens of plasminogen from healthy persons, on a double logarithmic scale against the percentage thinning. The points plotted then produce an approximately straight line.

DESCRIPTION OF THE PREFERRED EMBODIMENTS

First Preferred Embodiment:

A practical example of the measurement process according to the invention is described below:

Antiplasmin-free plasma is first prepared. Citrate plasma is shaken approximately 1 min. with 3 parts isoamylalcohol and then centrifuged at 3000 r.p.m. for about 30 minutes. The residue is siphoned off and thrown away. A further centrifugation for approximately 30 minutes at about 4° C is then required. After this, the remaining residue is thrown away. The measurement itself is effected as follows:

A definite amount of fibrinogen (for example, 0.1 ml of human fibrinogen free of plasminogen obtained from Behringwerke in a concentration of 200 mg%) is selected in advance. A specimen of antiplasmin-free patient's plasma is added to this (for example, 0.1 ml) followed by a plasminogen activator (for example, 1 E Urokinase in 0.1 ml). After a constant activating time (for example, 30 sec. at 37° C), thrombin (for example, test thrombin of the Company Behringwerke 0.3 E in 0.1 ml) is added and the automatic counter of the coagulator is set in motion. The plasminogen content applicable to the time of measurement is read out as a percentage on the calibration curve previously mentioned.

The advantages which can be obtained from the process according to the invention include the fact that the usual coagulometers provided in the majority of clinics can be used for carrying out the process. The test is also very simple to perform, so that it can be carried out in the laboratories of medical technical assistants. The reduction of the time of measurement in contrast to the known process referred to in the introduction to this specification renders the process of the invention suitable for routine purposes. In addition, the process of the invention is notably cheaper.

By the process of the invention it is possible to conduct tests using standard clinical diagnosis equipment in the form of purchasable test sets so as, for example, by dosage of streptokinase according to the extent of the actual plasminogen level, to improve the method of therapy and to reduce complications.

By adding streptokinase, the plasminogen is activated and thus, by means of streptokinase, the coagulation time can be delayed by plasmin formation in a booster reaction in a fibrinogen solution not sensitive to streptokinase, for example non-human fibrinogen, which does not contain human plasminogen. The method of converting the plasminogen of the specimen (by an excess of streptokinase into the activator PP-SK-Complex), of placing the activator formed in an insensitive system for the streptokinase excess above the plasmin formation (booster reaction), and of thus measuring the dissolution of the coagulum, is discussed in literature (for example, the modified clot lysis method of Christensen). This method is too costly for routine measurements.

COMPARISON OF PREFERRED EMBODIMENTS

If streptokinase is used as a plasmin activator instead of, for instance, the well-known urokinase, a method is obtained which is adequately usable for clinical routine. This, however, has a series of severe disadvantages. Streptokinase must be dissolved and added to the thinned specimen. A constant activating time must be maintained and the specimen subsequently processed at once. Variations bring about a fairly large error in measurement. Only a small amount of the treated specimen can be processed. Thus, a lot of streptokinase, which is very expensive, is lost.

After adding the activator thus formed to the fibrinogen solution, a second reaction time must be terminated accurately, before the thrombin starts up the coagulating reaction. If it is wished to reduce the activating time and the second reaction time is to be maintained uniform when using streptokinase so as to arrive at the desired measurement more quickly and exactly, and to reduce simultaneously the amount of streptokinase, so as to economise on costs, it may be an advantage to use as the plasmin activator streptokinase contained in the fibrinogen solution before plasma is added to the latter. In this case, there is thus already a constant dose of non-human streptokinase in the fibrinogen solution.

SECOND PREFERRED EMBODIMENT:

This method is described below more fully with the help of an example:

Preparation of a sufficiently antiplasmin-free specimen of plasma is effected (by the method according to Christensen) at a dilution of 1 : 20. A specimen of this dilution, for example 0.2 ml, is added to, for instance, 0.4 ml of a stock solution consisting of, for example, cattle fibrinogen (for example, 400 mg%) plus cattle plasminogen plus streptokinase (for example 1,000 E/ml) After a preselected activation time, thrombin is added and the coagulation time measured.

In this way, the two reactions, i.e. plasmin activation and bread-down of fibrinogen are combined in one operation. With a dilution of the specimen plasma of 1 : 20 and subsequent processing of 1/20 of the volume, the required dose of streptokinase can thus be reduced to 1/20. Measuring accuracy is improved by the single measuring time. The streptokinase is preferably kept as a dry substance, the as yet undissolved fibrinogen matter is stored separately, and streptokinase and fibrinogen are brought into solution in one operation by addition of a solvent.

What I claim is:

1. The process of measuring the plasminogen content of a plasma sample comprising the steps of:
  a. eliminating any antiplasmin from the plasma sample,
  b. adding a predetermined amount of fibrinogen to the sample,
  c. adding an amount of plasminogen activator sufficient to activate all possible plasminogen present in the sample, and
  d. incubating the sample a sufficient period of time to form a solution of fibrinogen and antiplasmin-free, plasminogen-activated plasma,
  e. adding thrombin to the solution, and
  f. timing the reaction until the moment of fibrin coagulation is observed in the solution, the plasminogen content to be established by comparing the observed time to fibrin coagulation with an established normal standard.

2. The process of measuring the plasminogen content of a plasma sample comprising the steps of:
  a. eliminating any antiplasmin from the plasma sample,
  b. adding a predetermined amount of fibrinogen to the sample,
  c. selecting a plasminogen activator from the group consisting of urokinase and streptokinase,
  d. adding an amount of the selected plasminogen activator sufficient to activate all possible plasminogen present in the sample,
  e. incubating the sample a sufficient period of time to form a solution of fibrinogen and antiplasmin-free, plasminogen-activated plasma,
  f. adding thrombin to the solution, and
  g. timing the reaction until the moment of fibrin coagulation is observed in the solution, the plasminogen content to be established by comparing the observed time to fibrin coagulation with an established normal standard.

3. The process of claim 2 wherein the antiplasmins are removed from the plasma sample in step (a.) by washing the sample with isoamylalcohol.

4. The process of claim 2 wherein the plasminogen activator used in step (c.) is urokinase.

5. The process of claim 2 wherein the plasminogen activator used in step (c.) is streptokinase.

6. The process of claim 5 wherein the streptokinase is added to the fibrinogen of step (b.) before the fibrinogen is added to the sample.

7. The process of claim 6 wherein an additional amount of plasminogen is added to the fibrinogen of step (b.) before the fibrinogen is added to the sample.

8. The process of claim 6 wherein the streptokinase and fibrinogen are stored before use in the dry state and are brought into solution together in one operation by the addition of a solvent.

* * * * *